US 7,090,812 B2

(12) United States Patent
Joyce et al.

(10) Patent No.: US 7,090,812 B2
(45) Date of Patent: Aug. 15, 2006

(54) PHASE TRANSFER CATALYSIS SCRUBBER

(75) Inventors: Peter J. Joyce, Mullica Hill, NJ (US); Roman Bielski, Coopersburg, PA (US); Terrence P. Buckmaster, Turnersville, NJ (US); Marc Halpern, Cherry Hill, NJ (US)

(73) Assignee: Value Recovery, Inc., Bridgeport, NJ (US)

( * ) Notice: Subject to any disclaimer, the term of this patent is extended or adjusted under 35 U.S.C. 154(b) by 185 days.

(21) Appl. No.: 10/446,753

(22) Filed: May 27, 2003
(Under 37 CFR 1.47)

(65) Prior Publication Data
US 2004/0126295 A1    Jul. 1, 2004

Related U.S. Application Data

(63) Continuation-in-part of application No. 10/236,382, filed on Sep. 6, 2002, now Pat. No. 6,846,946.

(51) Int. Cl.
*C01B 17/20* (2006.01)
(52) U.S. Cl. .................. 423/242.2; 570/101; 422/177
(58) Field of Classification Search ............. 570/101; 423/240
See application file for complete search history.

(56) References Cited

U.S. PATENT DOCUMENTS

| | | |
|---|---|---|
| 4,211,761 A | 7/1980 | Tung |
| 4,324,775 A | 4/1982 | Tung |
| 5,213,604 A | 5/1993 | Saito et al. |
| 5,419,885 A | 5/1995 | Doran et al. |
| 5,481,042 A | 1/1996 | Burba, III et al. |
| 5,681,470 A | 10/1997 | Safi |
| 5,904,909 A | 5/1999 | Yates et al. |
| 6,051,198 A | 4/2000 | Sano et al. |
| 6,106,853 A | 8/2000 | Cox et al. |
| 6,207,120 B1 | 3/2001 | Belmonte et al. |

OTHER PUBLICATIONS

Bielski et al., Abstract of Paper American Chemical Society, 2002, 224, No. 78.*
Bielski et al., 2002, CAS:PREV200200490999.*
Jianying Gan, Scott R. Yates; "Recapturing and decomposing methyl bromide in fumigation effluents"; Journal of Hazardous Materials S7, 1998; pp 249-258; Elsevier Science B.V.
J. Gan, S.R. Yates, J.O. Becker; "Ammonium Thiosulfate Fertilizer Reduces Methyl Bromide Emissions From Soil"; 2 pp; http://www.ars.usda.gov/is/np/mba/july98/ammonium.htm Jul. 16, 2003.
James G. Leesch, Gerhard F. Knapp; "Trapping/Destroying Methyl Bromide on Activated Carbon Following Commodity Fumigation"; MEBR Newsletter, Oct. 1998, 2 pp.
Laurence G. Miller, Shaun M. Baesman, Ronald S. Oremland; "Bioreactors for Removing Methyl Bromide following Contained Fumigations"; Environmental Science & Technology, vol. 37, No. 8, 2003; pp 1698-1704.
Jon D. Snyder, James G. Leesch; "Methyl Bromide Recovery on Activated Carbon with Repeated Absorption and Electrothermal Regeneration"; Ind. Eng. Chem. Res. 2001, 40; pp 2925-2933; American chemical Society.
A. R. Loch, K. A. Lippa, D. L. Carlson, Y. P. Chin, S. J. Traina, A. L. Roberts; "Nucleophilic Aliphatic Substitution Reactions of Propachlor, Alachior, and Metolachlor with Bisulfide ($HS^-$) ($S_n^{2-}$)"; Environmental Science & Technology, vol. 36, No. 19, 2002; pp 4065-4073; American Chemical Society.
Maw-Ling Wang, Yao-Hsuan Tseng; "Phase-transfer catalytic reaction of dibromo-o-xylene and 1-butanol in two-phase solution"; Journal of Molecular Catalysis A; Chemical 179 (2002); pp 17-26; Elsevier Science B.V.
Mordecai Rabinovitz, Yoram Cohen, Marc Halpern; "Hydroxide Ion Initiated Reactions Under Phase Transfer Catalysis Conditions: Mechanism and Implications"; Angew. Chem. Int. Ed. Engl. 25 (1986), pp 960-970.
Branko Juršić; "Synthetic Application of Micellar Catalysis. Williamson's Synthesis of Ethers"; Tetrahedron vol. 44, No. 21, 1998; pp 6677to 6680; Pergamon Press plc.
Domenico Albanese, Dario Landini, Angelamaria Maia, Michele Penso; "Key Role of Water for Nucleophilic Substitutions in Phase-Transfer-Catalyzed Processes; A Mini-Review"; Ind. Eng. Chem. Res. 2001, vol. 40; pp 2396-2401; American Chemical Society.

* cited by examiner

Primary Examiner—Taofiq Solola
Assistant Examiner—Robert Shiao
(74) Attorney, Agent, or Firm—RatnerPrestia

(57) ABSTRACT

A method and system for reactively destroying alkyl halides in volume or stream of gas. The method and device employ nucleophilic reaction of the alkyl halide under phase transfer catalysis conditions. The method and system are useful for scrubbing applications requiring the reduction of alkyl halide concentrations to very low levels.

24 Claims, 4 Drawing Sheets

Table 1
Sampling Data of Value Recovery Scrubbing System at U Florida Fumigation Field Test 28-Feb-03

| Run Time Hrs | Sample No. | Flowrate cc/min | Trailer Loading Oz/Ft^3 | Trailer Loading ppm | Sample Reading ppm | Actual ppm | Percent Removed | Comments |
|---|---|---|---|---|---|---|---|---|
| 0.0 | na | 170 | 320 | 82560 | na | na | na | Start MeBr Feed |
| 0.3 | 1 | 185 | 320 | 82560 | 30 | 7.5 | 99.991% | |
| 0.8 | 2 | 170 | 320 | 82560 | 15 | 3.8 | 99.995% | |
| 1.3 | 3 | 175 | 314 | 81012 | 13 | 3.3 | 99.996% | Halfway between 10 and 15 |
| 1.8 | 4 | 250 | 310 | 79980 | 10 | 2.5 | 99.997% | Flowrate above 250 |
| 3.1 | 6 | 250 | 284 | 73272 | 8 | 2.0 | 99.997% | |
| 3.4 | 7 | 250 | 284 | 73272 | 7 | 1.8 | 99.998% | |
| 3.7 | 8 | 250 | 284 | 73272 | 8 | 2.0 | 99.997% | Written as 5 to 10 ppm |
| 4.0 | 9 | 250 | 284 | 73272 | 8 | 2.0 | 99.997% | |
| 4.8 | 10 | 250 | 284 | 73272 | 50 | 12.5 | 99.983% | Breakthrough |
| | | | | | Avg | 4.1 | 99.995% | |

Notes:
Run Started at 3:55 PM
All samples used 4 pumps from Kitagawa Tube Syringe Pumps, Sample data is divided by 4 per instructions
Sample No. 5 tube was damaged and not used
Trailer Loading is Methyl Bromide Concentration taken from the average of two readings

FIG. 4

PHASE TRANSFER CATALYSIS SCRUBBER

CROSS REFERENCE TO RELATED APPLICATIONS

This application is a continuation in part of U.S. application Ser. No. 10/236,382, filed Sep. 6, 2002 now U.S. Pat. No. 6,846,946.

FIELD OF THE INVENTION

This invention relates to removal of pollutants from a gas. More particularly, this invention relates to removal and destruction of alkyl halides from a gas.

BACKGROUND OF THE INVENTION

Many alkyl halides possess a degree of toxicity, sometimes very high toxicity. For example, the toxicity of methyl bromide is so great that it has been used for many years in the extermination of insects in mills, warehouses, vaults, ships, freight cars, and also as a soil fumigant for use by growers of strawberries, tomatoes, and other crops. Other applications include treatment of ships to remove rodents and treatment of foods such as fruits including dried fruits, grain, flour, nuts, and tobacco products to remove potential pests. Additionally, methyl bromide has been successful in fumigation against various microorganisms including fungi and bacteria. Recently, it has been advocated as the most effective agent against anthrax (*Bacillus anthracis*). Its virtues include the fact that it is not explosive, practically nonflammable, has excellent permeability, and has been used safely for over 60 years.

Unfortunately, the release of methyl bromide into the atmosphere is strongly suspected of causing ozone layer depletion that can result in increased incidences of skin cancer. Thus there is a need for methods of disposing of methyl bromide without releasing it to the atmosphere. In addition, there is a more general need for methods of rapidly and economically removing volatile alkyl halides such as methyl bromide from streams such as air or petroleum vapors.

Prior art methods for removal of alkyl halides can be divided into nondestructive and destructive ones. Most such methods in either category are not satisfactory for rapid removal of alkyl halides from gaseous streams and/or air volumes.

Non-destructive Methods of Alkyl Halide Removal

Non-destructive methods of alkyl halide removal typically involve either scrubbing by dissolution of the halide in an appropriate solvent, or by adsorption onto a suitable adsorbent. Scrubbing solvents that work by dissolution of the alkyl halide include for example vegetable oil and marine oil (Canadian Patent 1,282,317). Examples of applicable adsorbing agents include zeolites (U.S. Pat. No. 4,309,281), and activated carbon J. G.

Leesch, G. Knapp, B. E. Mackey, Methyl Bromide Adsorption on Activated Carbon to Control Emissions from Commodity Fumigations, www.nal.usda.gov/ttic/tektran/data/000008/58/0000085839.html, also: J. G. Leesch, G. Knapp, B. E. Mackey, J. Stored Prod. Res., 36, 65, 2000). Methods based on the use of adsorbents or scrubbing solvents suffer from non-discriminatory scrubbing of other volatile compounds in the gas streams, resulting in the formation of unwanted degradation products during regeneration of the adsorbent or scrubbing solvent.

Destructive Methods of Alkyl Halide Removal

Japanese Kokai JP 49127862 discloses a method involving a reaction of methyl bromide in isopropanol with ethanolamine dissolved in water. The method takes advantage of a nucleophilic substitution reaction that is, however, not sufficiently rapid for a variety of applications. Another method employs bioreactors and specific species of a-Proteobacteria that can directly oxidize and grow on methyl halides (L. G. Miller, S. M. Baesman, R. S. Oremland, Use of Bioreactors to Remove Methyl Bromide Following Contained Fumigations, Proceedings of 2002 Annual International Research Conference on Methyl Bromide Alternatives and Emissions Reductions; also: L. G. Miller, S. M. Baesman, R. S. Oremiand, Bioreactors for Removing Methyl Bromide following Contained Fumigations, Environ. Sci. Technol., 37, 1698, 2003). Yet another destructive method (F. G. Belmonte, K. J. Abrams, J. P. Oppenheim, U.S. Pat. No. 6,207,120 B1; Mar. 27, 2001) proposes to heat and mix a vent gas containing an alkyl halide with a combustible fluid, followed by catalytic oxidation of the mixture.

Despite these advances, there continues to be a need for rapid and efficient means for removing alkyl halides at low and moderate concentrations from gas streams.

SUMMARY OF THE INVENTION

In one aspect, the invention is a method of removing an alkyl halide from a gas stream. The method comprises contacting the gas stream with a mixture comprising water, a phase transfer catalyst, and a nucleophile.

In another aspect, the invention is a method of removing methyl bromide from a gas volume. The method comprises withdrawing a gas stream from the gas volume and contacting the gas stream with a mixture comprising water, a phase transfer catalyst, and a nucleophile, thereby producing a purified gas stream.

In yet/another aspect, the invention is a system for removing methyl bromide from a gas volume. The system comprises a reactor assembly comprising a reaction vessel containing a mixture comprising water, a phase transfer catalyst, and a nucleophile; and a gas stream feed tube for removing a gas stream from the gas volume and directing it to the reactor assembly. The reactor assembly is adapted to provide contact of the gas stream with the mixture, thereby forming a purified gas stream.

It has now been found that the use of phase transfer catalysis conditions to accelerate the reaction of alkyl halides with certain reactive species provides a rapid and effective way of removing alkyl halides from a gas stream or volume.

BRIEF DESCRIPTION OF THE DRAWINGS

FIG. 4 is a table of test results showing removal of methyl bromide, according to the invention.

DETAILED DESCRIPTION OF THE INVENTION

The present invention provides a method of permanently removing alkyl halides from a gas stream or gas volume, for example an air stream or air volume. As used herein, the terms "gas volume" and "air volume" refer to any body of gas or air, respectively, whether contained or not contained. According to the invention, a phase transfer catalyst is used to assist transfer of a nucleophile from an aqueous phase to an organic phase in contact with it (or to the aqueous-organic interface) which contains an alkyl halide and, optionally, an organic solvent. Methods and devices according to the present invention may be applied either on a batch or continuous basis.

Phase transfer catalysts are used in a wide variety of chemical processes where one or more phase boundaries exist and one or more constituents cross a phase boundary. A phase transfer catalyst is capable of transferring a reactant from one phase into another phase in which a second reactant is located and in which the first reactant, after transfer, is available for reaction in the organic phase. After reaction of the two species, the phase transfer catalyst recycles back to the first phase, to once again transfer some of the first reactant to the second phase. Such phase transfer catalysts are described in Starks, C., Liotta, C., Halpern, M.; "Phase Transfer Catalysis Fundamentals, Applications and Industrial Perspectives", Chapman and Hall, 1994, incorporated herein by reference.

Thus, phase transfer catalysis (PTC) facilitates intimate contact of reactants that, usually because of phase solubility limitations, would not normally interact efficiently. Phase transfer catalysis allows these reactions to proceed more quickly and/or at lower temperatures, and sometimes with great selectivity.

The invention will next be illustrated with reference to the figures, wherein the same numbers indicate the same elements in all figures. Such figures are intended to be illustrative rather than limiting and are included herewith to facilitate the explanation of the present invention. The figures are not to scale, and are not intended to serve as engineering drawings.

Figure 1:
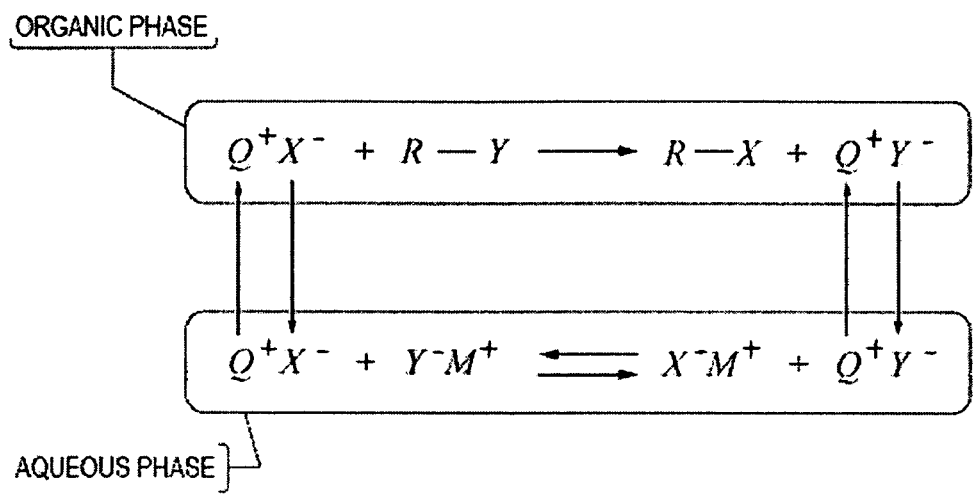
FIG. 1 is a schematic illustration of a typical mechanism of phase transfer catalysis, according to the prior art.

Referring now to FIG. 1, there is shown in schematic form a generalized description of how a typical PTC system works in many cases to assist a nucleophilic reaction, according to the prior art. The mechanism shown is known as the Starks Extraction Mechanism. In this representation, the phase transfer catalyst, which may for example be a quaternary ammonium salt, is denoted as $Q^+Y^-$. (Note that, although the anion of the quaternary ammonium salt is shown here for simplicity as the same as the leaving group anion formed by the reaction of R—Y, it can be a different anion.)

One of the reactants is a water-soluble nucleophile, such as an anion denoted as $X^-$. The organic substrate, identified as R—Y (an alkyl halide in the present invention, with Y=halogen), is typically soluble in an organic phase and not very soluble in water, hence the need for a specific catalyst system to bring the reagents together. The organic phase may contain solvent, or it may consist solely of the phase transfer catalyst itself. The product of the reaction between the alkyl halide and the nucleophile is denoted as R—X. In this organic-aqueous liquid-liquid system, the positively charged catalyst cation ($Q^+$) pairs in the aqueous phase or at the aqueous-organic interface with the water-soluble anion ($X^-$), and this complex ($Q^+X^-$) crosses the aqueous-organic interface as shown in FIG. 1. In this way, the positively charged catalyst cation ($Q^+$) delivers the anion to the organic phase, where it undergoes an irreversible reaction with the alkyl halide (R—Y) to produce the desired product R—X.

The liberated leaving group anion, $Y^-$, pairs with the quaternary ammonium cation to form the ion pair $Q^+Y^-$ as mentioned above and shown in FIG. 1, and is thereby distributed between the aqueous and organic phases. Thus the quaternary ammonium cation $Q^+$ and the leaving group anion $Y^-$ can migrate back to the aqueous phase by a reversible mechanism (either from the organic phase or the aqueous-organic interface) where $Q^+$ can again pair up with another nucleophilic anion to regenerate $Q^+X^-$. It should be noted that, in some phase transfer catalysis systems, the complex ($Q^+X^-$) does not move into the organic phase but undergoes the reaction with the organic substrate at the organic-aqueous interface. In addition, the reaction may also occur to some degree in the aqueous phase.

Figure 2:
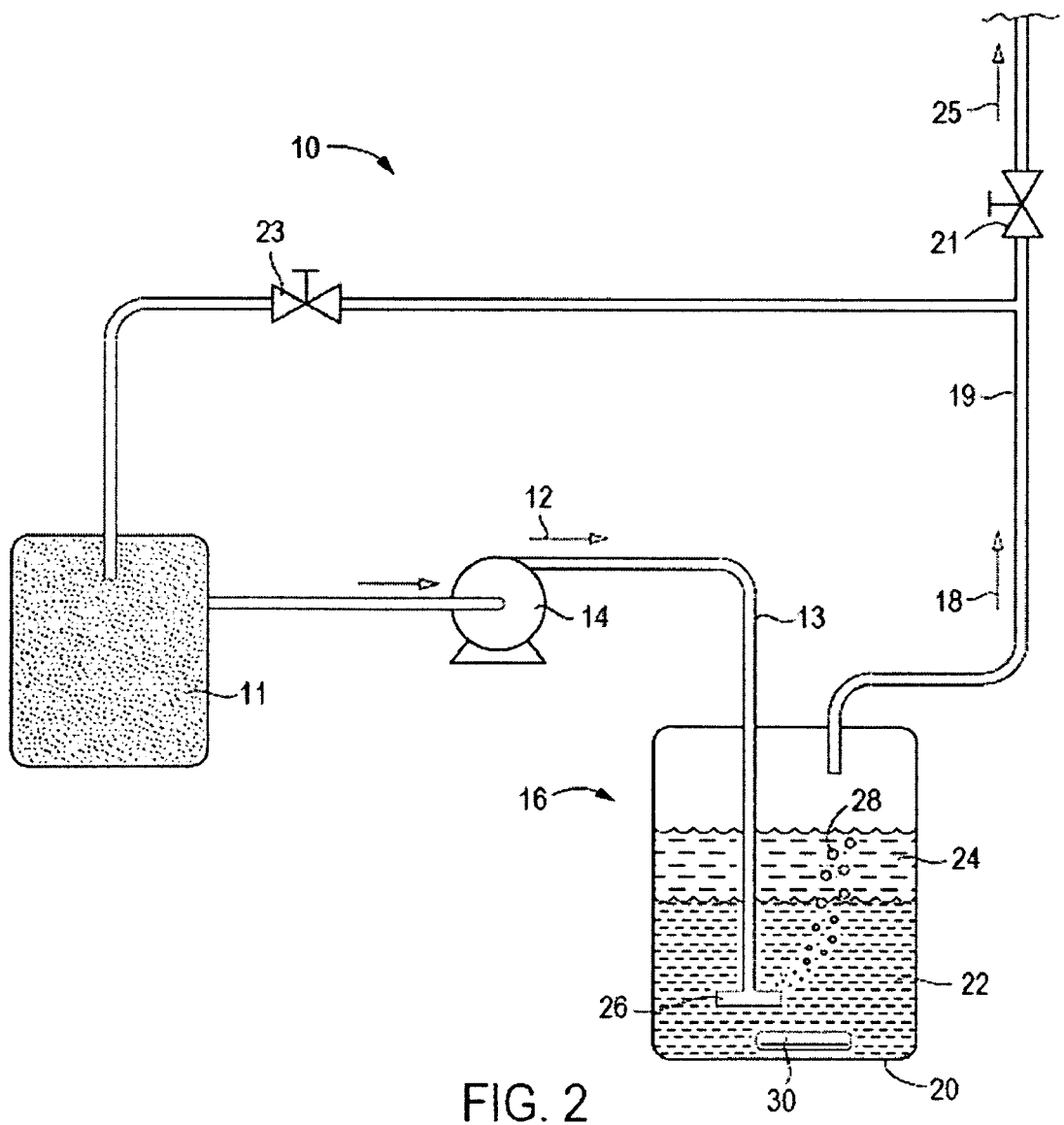
FIG. 2 is a schematic illustration of a gas scrubbing system according to one exemplary embodiment of the invention.

Attention is now drawn to FIG. 2, which shows a gas scrubbing system according to one exemplary embodiment of the invention. The gas scrubbing system, indicated generally at 10, comprises a gas volume 11 containing a gas having some amount therein of an alkyl halide, typically in the vapor phase but possibly as droplets or as part of other suspended particles. Gas volume 11 may be an unconfined region of gas, or it may be a gas contained within a house or other habitable structure, a fumigation chamber, or within a temporary enclosure such as may be constructed from tarpaulins covering an area of crops or the like. Gas volume 11 may also be in a tank or similar gas-handling container.

A gas stream 12 is pulled from the gas volume by pump 14 through gas stream feed tube 13, and delivered to reactor assembly 16. Although a pump is shown for item 14, a fan or other air-moving device may be used. Also, while the embodiment shown in FIG. 2 shows pump 14 being situated upstream of reactor assembly 16, the placement of the pump is not an important design feature, and the pump could be downstream of the reactor assembly. A purified gas stream 18 exits from reactor assembly 16 through purified gas stream return tube 19. By appropriate use of valves 21 and 23, purified gas stream 18 may be delivered back to gas volume 11, or it may be delivered to vent 25, which may lead to the atmosphere or into a product tank or other enclosure, or into another scrubber. Although a single reactor assembly 16 is shown in FIG. 2, two or more may be used, and they may be connected in parallel and/or in series.

Reactor assembly 16 comprises a reaction vessel 20 containing an aqueous phase 22 and an organic phase 24. Reaction vessel 20 may be of any convenient shape and appropriate material of construction. Although aqueous phase 22 is shown below organic phase 24, embodiments having the opposite orientation may also be used, for example if the organic phase is denser than the aqueous phase. In the embodiment shown in FIG. 2, gas stream 12 passes into aqueous phase 22 through a gas disperser 26, for example a glass frit that provides introduction of small bubbles of feed gas into the liquid to enhance the overall gas-liquid mass transfer rate. Other types of gas disperser may also be used, for example a pipe with holes in it, or a plate with holes in it, or any other device known in the art to convert the gas stream into small bubbles. Bubbles 28 rise and pass through the aqueous and organic phases, providing contact such that the alkyl halide is efficiently dissolved in one or both of these phases. An optional agitator 30 may be used to increase contact between the aqueous and organic phases, thereby facilitating the transfer of reactants from one to the other. It is preferred that the bubbles 28 be small, so as to increase the rate at which alkyl halide is carried into aqueous phase 22 and/or organic phase 24 to the point where gas-liquid mass transfer is not the rate-limiting step in the reaction of alkyl halide with nucleophile.

FIG. 2 shows a magnetic stirring bar as agitator 30, but any agitation means may be used. One embodiment of the invention does not rely on any mechanical stirring, but takes advantage of the turbulence created in the liquid phase due to the introduction of the gas through the small openings in the frit. Aqueous phase 22 and/or organic phase 24 may be recycled or discarded when the nucleophile (discussed below) has been depleted due to reaction with the alkyl halide. Phases 22 and 24 may also be treated with appropriate reagents after scrubbing has been completed, for example to minimize toxicity or odor, and/or purified gas stream 18 may be treated for these or other purposes.

In the case where gas volume 11 comprises methyl bromide, a wide range of concentrations of methyl bromide may be scrubbed effectively, according to the invention. Thus for example, methyl bromide in air having a concentration of from 1 ppm to 99% by volume may be efficiently scrubbed. More typically, the concentration may be from about 25 ppm to about 10% by volume, most typically about 1.2% to about 2.4% by volume. Moreover, methyl bromide in these various concentration ranges in other gases, for example hydrocarbon gases, may be effectively scrubbed as well, according to the invention.

Figure 3:
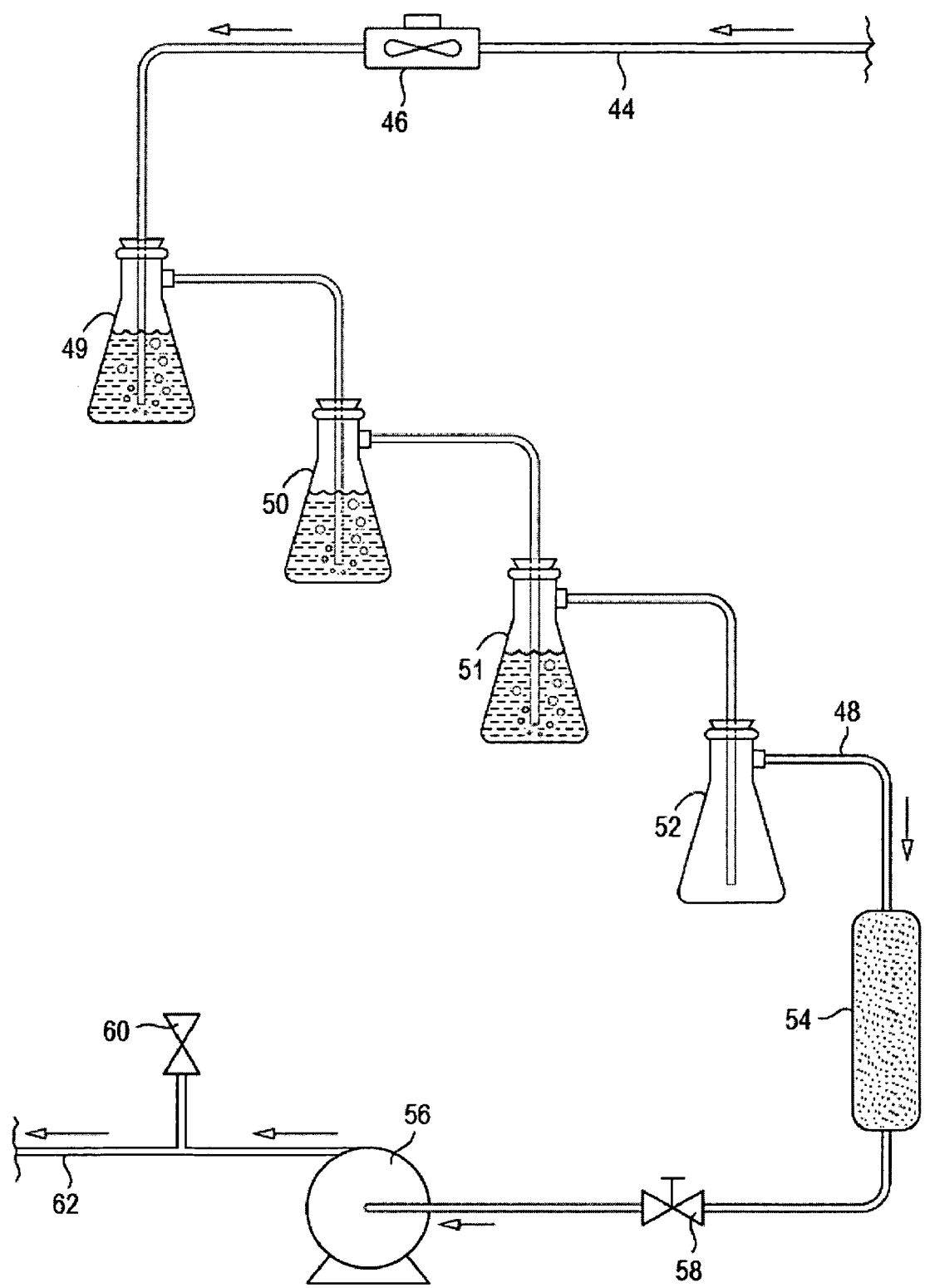
FIG. 3 is a schematic illustration of a gas scrubbing system according to another exemplary embodiment of the invention.

FIG. 3 shows another embodiment of the invention, in which a gas stream flows along path 44, through a flow meter 46, into three reactor assemblies 49, 50 and 51. The reactor assemblies may be constructed according to the description of the embodiment described in relation to reactor assembly 16 shown in FIG. 2 detailed above. The three reactor assemblies are connected in series, such that partially purified gas exiting reactor assembly 49 enters reactor assembly 50 for further purification, and the resultant further purified gas is yet further purified by reactor assembly 51. Although three reactor assemblies are shown, any number may be used. Additionally, although reactor assemblies 49, 50 and 51 are connected in series in the embodiment shown in FIG. 3, they may be connected in parallel, or in a combination of series and parallel connections.

At the output of the third reactor assembly is an empty gas washing bottle 52, which captures droplets of liquid entrained in the purified gas steam exiting the third reactor assembly. Although an empty gas washing bottle is used in the present embodiment, other devices known in the art for removing entrained droplets of liquid may be used. The purified gas stream passes along path 48 through optional desiccating unit 54, which may for example be a cylinder containing a desiccant such as calcium sulfate. The flow of gas through the entire system is regulated by use of throttling valve 58 in conjunction with pump 56, and samples of the purified gas output may be taken at optional sample port 60. The purified gas exits along path 62 to any of the destinations discussed above in relation to purified gas stream 18 in FIG. 2.

Aqueous Phase 22

Aqueous phase 22 contains a nucleophile, by which is meant an anion or molecule having a high electron density which is accessible for reaction with another molecule by displacement of a leaving group, typically an anion such as halide. Due to the presence of a good leaving group (halide anion), alkyl halides can take part in nucleophilic substitution reactions, typically (but not necessarily) of the bimolecular ($S_N2$) type.

Many neutral and anionic nucleophiles can participate in phase transfer catalysis-aided nucleophilic substitution reactions with alkyl halide, according to this invention. A non-limiting list of anions suitable for use as nucleophiles according to the invention includes the following and their derivatives: cyanide ($CN^-$), thiocyanate ($SCN^-$), cyanate ($OCN^-$), hydrogen sulfide ($HS^-$), sulfide ($S^{2-}$), carbonate ($CO_3^{2-}$), hydrogen carbonate ($HCO_3^-$), thiocarbonates (monothio, dithio, and trithio), azide ($N_3^-$), sulfite, hydrogen sulfite, sulfate, hydrogen sulfate, alkyl, aryl, or aralkyl thiolate, nitrite, nitrate, phosphates (mono and di hydrogen phosphates plus phosphate), thiophosphates, hydrogen selenide ($HSe^-$), selenide ($Se^{2-}$), benzenesulfonate, chloride, bromide, fluoride, iodide, trichloroacetate ($CCl_3COO^-$), thiosulfate, thiophosphate, chlorate, hypochlorite, malonate, dichloroacetate, chloroacetate, terephthalate, adipate, lactate, silicates, bromate, periodate, performate, m-chloroperbenzoate, formate, acetate, acrylate, propionate, butyrate, benzoate, furoate, oxalate, phthalate, hydrogen phthalate, phenolate, cresolate, and catecholate. Suitable neutral nucleophiles may include for example ammonia and primary, secondary, and tertiary amines, where the substituents on nitrogen may be any combination of alkyl, aryl, and aralkyl groups, and phosphines analogous to such amines. In this context, the term "derivative" means a compound that contains one of the nucleophilic groups listed above.

Particularly suitable nucleophiles for use according to the invention include compounds containing sulfur or nitrogen at the nucleophilic center. As used herein, the term "nucleophilic center" means that atom which becomes bonded to the alkyl halide residue by virtue of the nucleophilic reaction. Specific examples of suitable sulfur nucleophiles include aliphatic and, preferably, aromatic thiols and their salts, aliphatic and aromatic disulfides and polysulfides, sulfide anion, hydrogen sulfide anion, thiosulfate anion, sulfite or bisulfite anion, and thiocyanate anion. In one exemplary embodiment of the invention, the nucleophile comprises at least one of sodium sulfide and sodium hydrogen sulfide at a concentration of from about 0.1 wt. % to the saturation limit in the aquous phase. When sulfur nucleophiles are used, it may be advantageous to oxidize the resulting reaction products, for example with sodium hypochlorite, to convert them to materials having less odor.

Other suitable nucleophiles are alkoxides, carboxylates, hydroxide, and selenium analogs of sulfur nucleophiles.

When a precursor species must be ionized to become a highly reactive nucleophile, for example when an alcohol or thiol or carboxylic acid must be converted to the corresponding anion, a pH-adjusting agent is used in such an amount as to ensure that the pH is raised to a level sufficient to ionize the chemical species, namely by removing a proton from the species and generating a negatively charged species in the aqueous phase. The required pH is dependent on the nature of the nucleophile, namely whether its conjugate acid is a strong or weak acid. For example, if the nucleophile is the anion of a weak acid, a relatively higher pH may be required in order to produce a sufficient concentration of the anion. Conversely, when the chemical species already exists as a nucleophilic anion or as a neutral compound that can act as a nucleophile, no pH-adjusting agent may be needed. When a pH adjusting agent is needed, the particular amount of the agent or base will vary depending on process conditions, but can be optimized easily by altering the concentration and determining its effect on yield, bearing in mind the ranges of excess molar concentrations set forth above.

According to the present invention, a pH-adjusting agent (if needed to produce suitable quantities of nucleophile) is used in an amount sufficient to provide an excess molar concentration of base in the range between −0.99 and 1.0, preferably between −0.25 and 0.5, more preferably between stoichiometric and 0.25, and most preferably between 0.01 and 0.1. As used herein, the term "stoichiometric" means the amount of base indicated by a balanced chemical equation to be necessary to convert all of the precursor species to the desired nucleophile. Thus, the "excess molar concentration of base" is the amount of base actually in the system above that which would be stoichiometrically required to neutralize ionizable hydrogen atoms, and is expressed herein as the difference between the actual concentration of base and the stoichiometric concentration divided by the stoichiometric concentration. Thus, a negative value of excess molar concentration of base contemplates that less than the stoichiometric amount.

A suitable pH for purposes of the invention is one at which a nucleophilic anion is present and is at least partially soluble in the aqueous solution, typically from pH 9 to 13.5. However, certain embodiments of the present invention may provide sufficient amounts of nucleophile even at lower pH values, even as low as a pH of about 1, depending on the nucleophile used.

It should be recognized that the pH as used herein refers to the pH in the aqueous phase. The pH adjusting agent may be added to the aqueous phase prior to contacting the organic phase, or afterwards. Any of a number of suitable pH adjusting agents may be used, but some typical ones are sodium hydroxide, potassium hydroxide, magnesium hydroxide, calcium hydroxide, lithium hydroxide, ammonium hydroxide, magnesium carbonate, calcium carbonate, tetraalkyl ammonium hydroxides, sodium and potassium carbonates, hydrogen carbonates, phosphates, similar salts, and mixtures thereof.

It may be advantageous to include a co-catalyst in the reaction. Such a co-catalyst serves to enhance the overall rate of conversion of alkyl halide to non-halide containing species. Typical co-catalysts may include sodium iodide, potassium iodide, and alkaline earth metal iodide species. They are preferably mixed in with the aqueous phase, either before mixing with the organic phase or afterwards.

Preferred nucleophilic reaction conditions for the destruction of alkyl halides depend on a number of factors, including the specific chemical species used, the organic substrate used, and the phase transfer catalyst used. In general, the time, temperature and agitation should be selected to cause the reaction in the organic phase to proceed rapidly. Suitable temperatures are typically from 10° C. to 200° C., preferably 10–80° C., and most preferably 30–70° C. As is well known, the choice of temperature is dictated by the kinetics of the reaction. Reactions that occur more slowly are preferably run at higher temperatures. Lower reaction temperatures may however be suitable or even preferable in some situations, provided only that the reaction rate of alkyl halide be sufficiently fast to achieve the desired degree of removal.

According to one exemplary embodiment of the invention, aqueous phase 22 comprises from about 10 wt. % to about 20 wt. % of sodium hydrogen sulfide dissolved in water. Such a composition is highly effective in reacting with alkyl halides, for example methyl bromide.

Organic Phase 24

The phase transfer catalyst may be any material capable of transferring the nucleophile from the aqueous phase to the organic phase or interface, to enhance a reaction between the nucleophilic anion and the electrophile. As used herein, the term "enhance" in this context shall mean increasing the rate or extent of a reaction which would have occurred even in the absence of the phase transfer catalyst, or enabling a reaction to occur which would not have occurred to any significant extent in the absence of the phase transfer catalyst. Non-limiting examples of suitable phase transfer catalysts include quaternary ammonium salts, quaternary phosphonium salts, quaternary arsonium salts, polyethylene glycols, ethers of polyethylene glycols, crown ethers, cryptands, tertiary amines, and phase transfer catalysts adsorbed on supports such as silica and clay and the like or bound to polymers.

In particular, suitable phase transfer catalysts include methyltrioctylammonium chloride, tetrabutylammonium bromide, tetrabutylammonium hydrogen sulfate, methyltributylammonium chloride, benzyltriethylammonium chloride, triethylamine, tributylamine, trioctylamine, tetrabutylphosphonium bromide, tetraphenylphosphonium bromide, 18-crown-6, dibenzo-18-crown-6, benzo-15-crown-5, polyethylene glycol with a molecular weight in the range of 300 to 3000, the dimethyl and dibutyl ethers of such polyethylene glycols, and tris(3,6-dioxaheptyl)amine (also known as TDA-1). Preferably, the phase transfer catalyst is selected from the group consisting of quaternary ammonium salts, quaternary phosphonium salts, crown ethers, cryptands and polyethylene glycols. More preferably, the phase transfer catalyst is a quaternary ammonium salt selected from the group consisting of methyltrioctylammonium chloride and tetrabutylammonium bromide. Most preferably, the phase transfer catalyst is methyltrioctylammonium chloride, which is commercially available from Cognis Corporation of Ambler, Pa. under the trademark Aliquat® 336, or Adogen® 464, available from Sherex Chemical Company, Inc. of Dublin, Ohio.

In many cases it is desirable that the organic phase be solvent-free so as to increase the concentration of the nucleophile in the organic phase. On the other hand, a solvent may be preferable when it is necessary to slow a reaction that otherwise goes too fast, for example resulting in undesirable heat generation. A solvent may also be useful if reduction of the viscosity of the organic phase is desired. Any of a wide variety of organic solvents may be used for such a purpose, with toluene and methyl isobutyl ketone being suitable examples. The weight ratio of organic to aqueous phase is not critical, but generally it is desirable to keep the ratio small. The organic phase: aqueous phase weight ratio is typically 1:10 or less (preferably 1:20 or less) if the nucleophile is sulfide anion or hydrogen sulfide anion, thiocyanate, thiosulfate, cyanide, cyanate, carboxylate, sulfonate, carbonate, nitrite, azide, and/or derivatives thereof.

It may be preferable to select compositions of aqueous phase 22 and organic phase 24 such that, upon agitation and passing bubbles through them, they do not form an emulsion that is difficult to separate, thereby impeding recycling or disposal of these phases. However, the formation of such emulsions is not detrimental to the destructive reaction of alkyl halides according to the invention, and may in some cases accelerate that reaction by virtue of providing a higher interface area for transfer of reactants from one phase to the other. In addition, the nucleophilic reaction may also occur to some degree in the aqueous phase itself.

In an exemplary embodiment of the invention, the phase transfer catalyst is present in a molar amount equal to from 1% to 50% of the moles of nucleophile present within reactor assembly 16.

EXAMPLE

A gas scrubbing system was assembled for treatment of an enclosed airspace containing methyl bromide in a trailer, in order to simulate the removal of the methyl bromide in concentrations such as would be suitable for fumigating anthrax spores. The trailer was attached to a gas stream feed tube (polytetrafluoroethylene, 5/16" in diameter, Thomas Catalog No. 9560F60), and a similar purified gas stream return tube. The feed tube was attached to the input side of the reactor assembly, which was in turn connected to the inlet of a Vacuum Pump—Oil free KNF Model No. 7240-0 (available from KNF Neuberger Inc. of Trenton, N.J.). The return tube was connected to the output side of the pump.

The reactor assembly consisted of three 500-cc gas washing bottles, available from ACE Glass of Vineland, N.J., Model No. 7166-26, each fitted with a "C" frit having 25–50 micron pore openings. The bottles were sealed with 29/42 connections and connected in series, with each containing a magnetic stirring bar and a scrubbing mixture prepared as follows.

A mixture consisting of sodium sulfide nonahydrate (575.0 g), sodium thiosulfate pentahydrate (60.0 g), and water (575 g) was prepared. To this mixture was added sodium hydroxide (50% w/w solution; 100.0 g), and water was added to bring the volume of aqueous phase to 3000 mL. About 375 mL of this aqueous phase and about 40 mL of an organic phase consisting of methyltrioctylammbnium chloride (sold by Cognis Corporation of Ambler, Pa. under the trademark Aliquat® 336) was transferred into each gas washing bottle.

The gas washing bottles were set on magnetic stir plates and stirred with magnetic stir bars at ambient temperature (about 80° F.). A throttling valve and rotometer were attached in line at the exit of the pump, to allow adjustment of airflow through the reactor assembly at ambient temperature, about 80° F.

An additional gas washing bottle (empty) was used as a trap for entrained droplets coming from the third (last) gas washing bottle. After the trap, the purified gas was passed through a desiccant tube containing Drierite™ calcium sulfate desiccant to remove water vapor, providing a dry sample to aid measurement of the methyl bromide content of the purified air stream by use of Kitagawa Tubes (see below). The methyl bromide content of the air in the trailer was measured by thermal conductivity, using a Fumiscope™, available from Key Chemical and Equipment Co., Clearwater, Fla.

Figure 5:
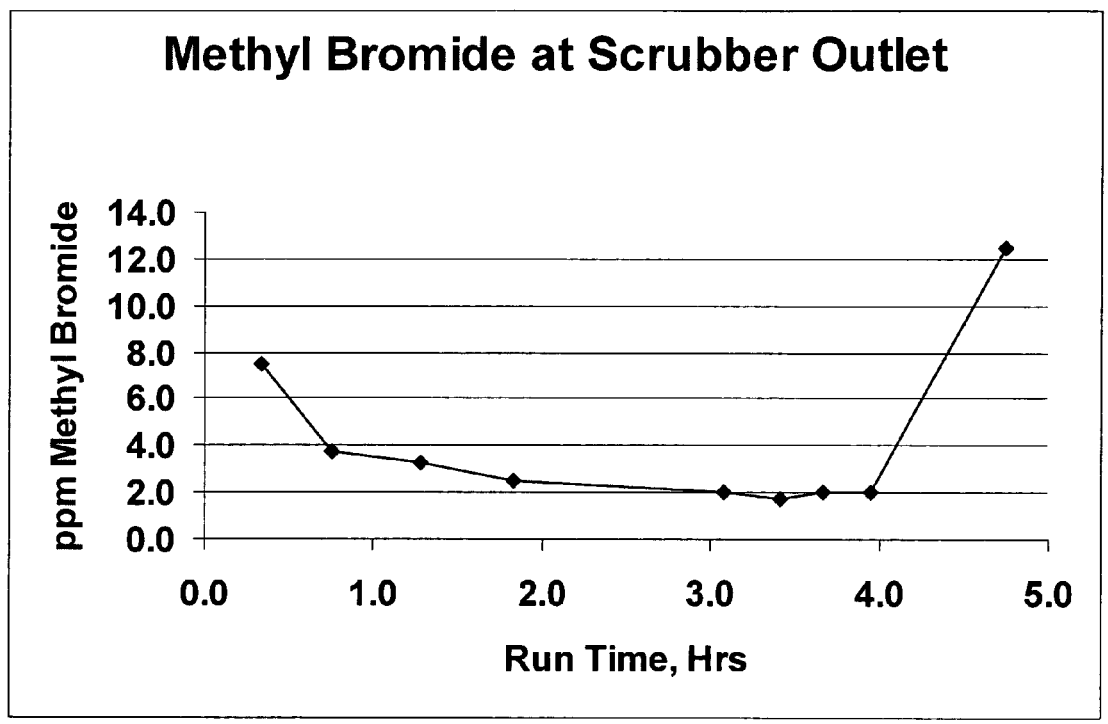
FIG. 5 is a plot showing the results of FIG. 4 in graphic format.

The pump and throttling valve were adjusted to pull 200 cc/min of air containing methyl bromide from the trailer through the gas washing bottles, at flow rates and methyl bromide concentrations as shown in FIG. 4. Sampling of the purified air stream exiting the reactor assembly 16, (using Kitagawa Precision Gas Detector Tubes, Tube No. 157SB, available from Matheson Safety Products, E. Rutherford, N.J.) prior to returning it to the trailer, indicated a concentration of about 2 ppm by volume of methyl bromide, as shown in FIGS. 4 and 5.

The average outlet concentration of methyl bromide was 4.1 ppm over 4.8 hours. At the beginning the inlet concentration decreased logarithmically and settled at a steady state value of 2 ppm in less than 2 hours. The overall average removal of methyl bromide was 99.995%.

Although the invention is illustrated and described herein with reference to specific embodiments, the invention is not intended to be limited to the details shown. Rather, various modifications may be made in the details within the scope and range of equivalents of the claims without departing from the invention.

What is claimed:

1. A method of removing an alkyl halide from a flowing gas, the method comprising contacting the flowing gas containing the alkyl halide with a mixture comprising water, a phase transfer catalyst, and a nucleophile selected from the group consisting of cyanide, thiosulfate, cyanate, carboxylate, nitrite, azide, sulfate, sulfide, hydrogen sulfide, and carbonate anions.

2. The method of claim 1, wherein the mixture consists essentially of water, a phase transfer catalyst, and a nucleophile.

3. The method of claim 1, wherein the mixture further comprises an organic solvent capable of diluting the phase transfer catalyst.

4. The method of claim 1, wherein the nucleophile comprises nitrogen at the nucleophilic center.

5. The method of claim 1, wherein the nucleophile comprises sulfur at the nucleophilic center.

6. The method of claim 1, wherein the nucleophile comprises an anion selected from the group consisting of sulfide, hydrogen sulfide, and cyanide, and the alkyl halide comprises methyl bromide.

7. The method of claim 1, wherein the nucleophile comprises an anion selected from the group consisting of sulfide, hydrogen sulfide, and thiosulfate anions, and derivatives thereof.

8. The method of claim 1, wherein the nucleophile comprises an anion selected from the group consisting of sulfide and hydrogen sulfide anions.

9. The method of claim 1, wherein the nucleophile comprises thiosulfate anion.

10. The method of claim 1, wherein the phase transfer catalyst comprises a tetrasubstituted phosphonium cation, wherein each of the substituents is independently an alkyl, aryl, or aralkyl group.

11. The method of claim 1, wherein the phase transfer catalyst comprises a tetrasubstituted ammonium cation, wherein each of the substituents is independently an alkyl, aryl, or aralkyl group.

12. The method of claim 1, wherein the phase transfer catalyst comprises a tetrabutylammonium cation.

13. The method of claim 1, wherein the phase transfer catalyst comprises a methyltrioctylammonium cation.

14. The method of claim 1, wherein the mixture further comprises iodide ion.

15. The method of claim 1, wherein the contacting is performed more than once.

16. The method of claim 1, wherein the alkyl halide comprises methyl bromide.

17. The method of claim 1, wherein the alkyl halide comprises methyl bromide and the nucleophile comprises an anion selected from the group consisting of nitrite, thiosulfate, and combinations thereof.

18. A method of removing methyl bromide from flowing air, the method comprising contacting the flowing air containing the methyl bromide with a mixture comprising water, a phase transfer catalyst comprising a tetraalkylammonium cation, and a nucleophile comprising at least one of sulfide anion and hydrogen sulfide anion.

19. The method of claim 18, in which the phase transfer catalyst comprises methyltrioctylammonium chloride, the nucleophile comprises at least one of sodium sulfide and sodium hydrogen sulfide, and wherein the at least one of sodium sulfide and sodium hydrogen sulfide is dissolved in the water at a concentration of from about 0.1 wt. % to a saturation limit.

20. The method of claim 19, in which the concentration is from about 10 wt. % to about 20 wt. %.

21. The method of claim 1 in which the phase transfer catalyst is present in a molar amount equal to from 1% to 50% of the moles of nucleophile.

22. A method of removing methyl bromide from a gas volume, the method comprising withdrawing a flowing gas from the gas volume containing the methyl bromide and contacting the flowing gas with a mixture comprising water, a phase transfer catalyst, and a nucleophile, thereby producing a purified flowing gas.

23. The method of claim 22, wherein the gas volume is an air volume, the flowing gas is flowing air, and the purified flowing gas is a purified flowing air.

24. The method of claim 23 further comprising returning the purified flowing air to the air volume.

* * * * *